United States Patent [19]

Mueller et al.

[11] Patent Number: 4,581,170
[45] Date of Patent: Apr. 8, 1986

[54] N-HYDROXYL PROTECTING GROUPS AND PROCESS AND INTERMEDIATES FOR THE PREPARATION OF 3-ACYLAMINO-1-HYDROXY-2-AZETIDINONES

[75] Inventors: Richard H. Mueller, Lawrenceville, N.J.; Jakob-Matthias Drossard, Regensburg; Peter H. Ermann, Donaustauf, both of Fed. Rep. of Germany

[73] Assignee: E. R. Squibb & Sons, Inc., Princeton, N.J.

[21] Appl. No.: 637,260

[22] Filed: Aug. 3, 1984

[51] Int. Cl.$^4$ .................. C07D 205/08; C07D 417/12; C07D 405/12; C07C 83/00
[52] U.S. Cl. ......................... 260/239 A; 260/245.4; 260/330.9; 564/301; 564/158; 564/159; 548/475
[58] Field of Search .............. 260/245.4, 239 A, 330.9

[56] References Cited

U.S. PATENT DOCUMENTS 4,337,197  6/1982  Gordon et al. ................ 260/239 A

OTHER PUBLICATIONS

Breaer, Chem. Abs. 101, 38265y.
"Synthesis of Prostaglandin Models and Prostaglandins by Conjugate Addition of a Functionalized Oranocopper Reagent", Kluge et al., Journal of American Chemical Society, vol. 94, 1972, p. 7827.

Primary Examiner—Mark L. Berch
Attorney, Agent, or Firm—Lawrence S. Levinson; Donald J. Barrack

[57] ABSTRACT

Processes for preparing the useful intermediates having the formula

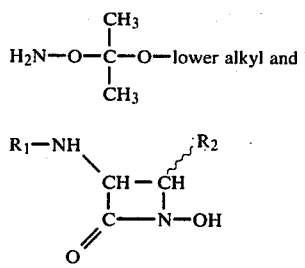

are disclosed herein, utilizing novel chemical compounds having the formula

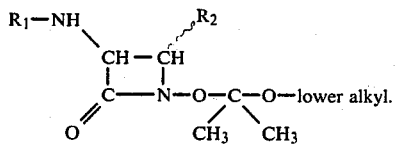

9 Claims, No Drawings

N-HYDROXYL PROTECTING GROUPS AND PROCESS AND INTERMEDIATES FOR THE PREPARATION OF 3-ACYLAMINO-1-HYDROXY-2-AZETIDINONES

RELATED APPLICATION

U.S. patent application Ser. No. 404,945, filed Aug. 4, 1982, now abandoned, discloses 3-acylamino-2-oxoazetidin-1-yloxy acetic acids having antibacterial activity.

BACKGROUND OF THE INVENTION

U.S. Pat. No. 4,337,197, issued June 29, 1982, discloses as antibacterial agents, 3-acylamino-2-oxo-1-azetidinyl sulfates. As intermediates for the preparation of these products, the reference discloses, inter alia, compounds having the formula

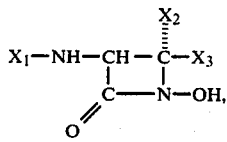

wherein $X_1$ is acyl and $X_2$ and $X_3$ are hydrogen or organic substituents including alkyl.

BRIEF DESCRIPTION OF THE INVENTION

This invention is directed to novel chemical compounds having the formula

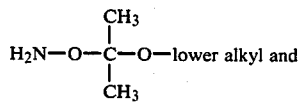

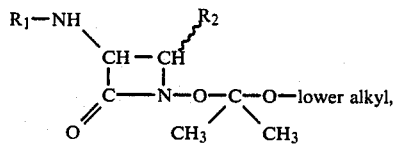

and to processes for using compounds of formula I and II to obtain compounds having the formula

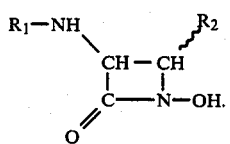

The compounds of formula III are useful as intermediates for the preparation of antibacterial agents; i.e., 3-acylamino-2-oxoazetidin-1-yloxy acetic acids, which are disclosed in U.S. patent application Ser. No. 404,945, filed Aug. 4, 1982, now abandoned, and 3-acylamino-2-oxo-1-azetidinyl sulfates, as disclosed in U.S. Pat. No. 4,337,197, issued June 29, 1982.

In formulas I, II and III, and throughout the specification, the symbols are as defined below.

$R_1$ is an acyl group derived from a carboxylic acid; and $R_2$ is hydrogen, lower alkyl or carbamoyloxymethyl.

The terms "lower alkyl" and "lower alkoxy", as used throughout the specification, refer to alkyl groups having 1 to 4 carbon atoms.

The compounds of formula II can be converted to the corresponding compound of formula III by simple treatment with a mild acid.

Alternatively, in those instances wherein $R_1$ is an acyl group derived from a carboxylic acid that is also an amino protecting group removable under neutral or basic conditions (referred to hereinafter as "$A_1$"), the compounds of formula II can be converted to the corresponding compound of formula III using the following reaction sequence:

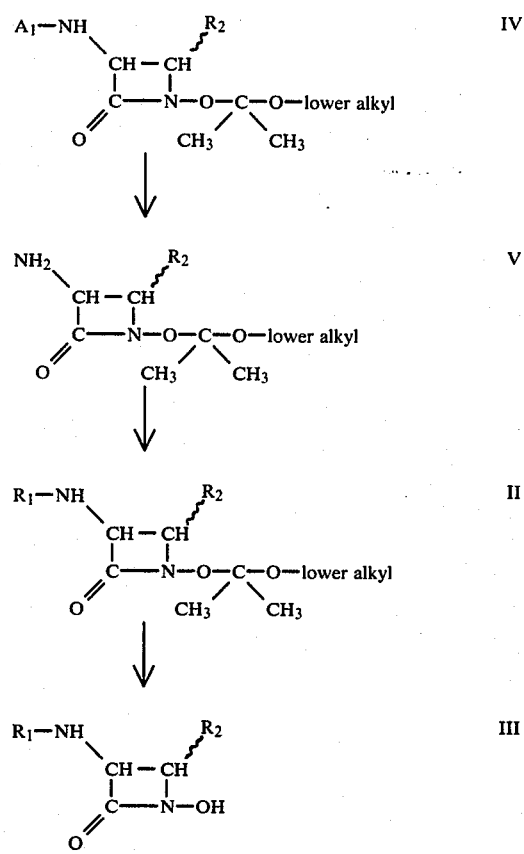

The expression "an amino protecting group that is removable under neutral or basic conditions" refers to any group which will protect the nitrogen atom to which it is attached from reacting in the above sequence, and which, at the end of the above-described reaction sequence can be cleaved from the nitrogen atom at a pH equal to, or greater than, 7.0. Exemplary of such groups are phenylmethoxycarbonyl and substituted phenylmethoxycarbonyl (e.g., phenylmethoxycarbonyl substituted with 4-methoxy, 4-chloro, 4-methyl, 2-methyl, 3-methyl, 2,4,6-trimethyl, 3,5-dimethoxy, 2-nitro, or 4-nitro), allyloxycarbonyl, cinnamyloxycarbonyl, vinyloxycarbonyl, 1,1-dimethylpropynyloxycarbonyl, 2-furanylmethyloxycarbonyl, 2-methylthioethyloxycarbonyl, 2-trimethylsilylethyloxycarbonyl, 2-methylsulfonylethyloxycarbonyl, 9-fluorenylmethyloxycarbonyl, 2,2,2-trichloroethyloxycarbonyl, 2-cyanoethyloxycarbonyl, and 1,1-dimethyl-2-cyanoethyloxycarbonyl.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian patent No. 867,994, published, Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British patent No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

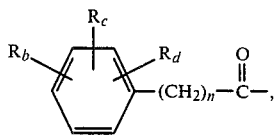

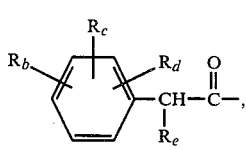

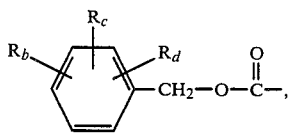

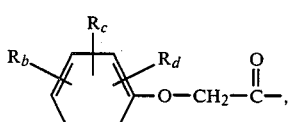

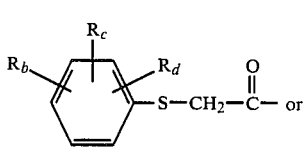

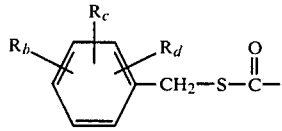

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

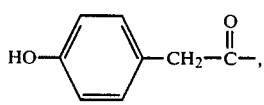

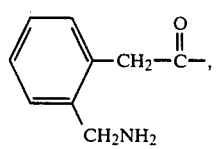

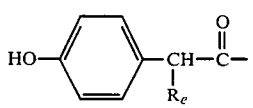

($R_e$ is preferably a carboxyl salt or sulfo salt) and

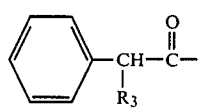

($R_e$ is preferably a carboxyl salt or sulfo salt).

(c) Heteroaromatic groups having the formula

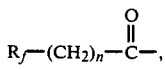

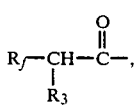

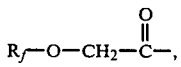

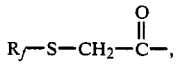

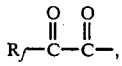

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

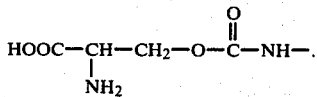

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, -furanyl, or 6-aminopyridin-2-yl.

(d) [[(4-Substituted-2,3-dioxo-1-piperazinyl)carbonyl]amino]arylacetyl groups having the formula

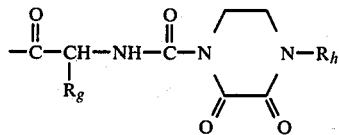

wherein $R_g$ is an aromatic group (including carbocyclic aromatics such as those of the formula

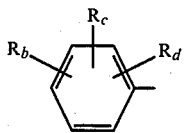

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

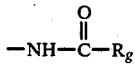

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino (e) (Substituted oxyimino)arylacetyl groups having the formula

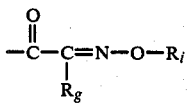

wherein $R_g$ is as defined above and $R_i$ is hydrogen, alkyl, cycloalkyl, alkylaminocarbonyl, arylaminocarbonyl (i.e.,

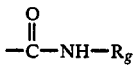

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

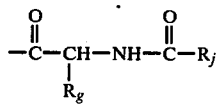

wherein $R_g$ is as defined above and $R_j$ is

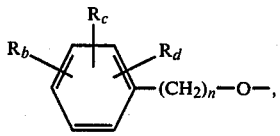

amino, alkylamino, (cyanoalkyl)amino, amido, alkylamido, (cyanoalkyl)amido,

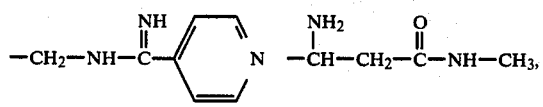

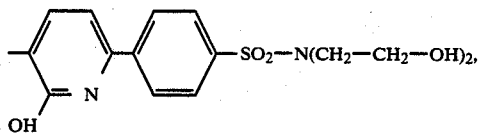

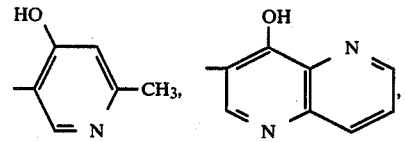

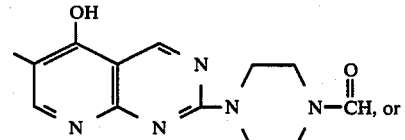

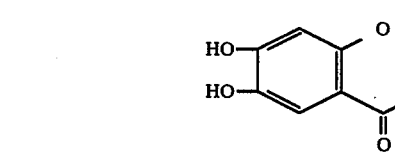

Preferred (acylamino)arylacetyl groups of the above formula include those groups wherein $R_j$ is amino or amido. Also preferred are those groups wherein $R_g$ is phenyl or 2-thienyl (g) [[[3-Substituted-2-oxo-1-imidazolidinyl]carbonyl-]amino]arylacetyl groups having the formula

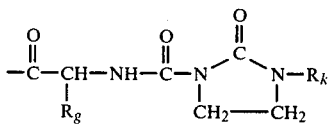

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups). Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

DETAILED DESCRIPTION OF THE INVENTION

The novel chemical compounds of formula I, II and IV, and the processes of this invention, are useful for the preparation of the hydroxamates of formula III. These hydroxamates can be used to prepare 3-acylamino-2-oxoazetidin-1-yloxy acetic acids and 3-acylamino-2-oxo-1-azetidinyl sulfates. As described in U.S. patent application Ser. No. 404,945, filed Aug. 4, 1982 and U.S. Pat. No. 4,337,197, issued June 29, 1982, these compounds are β-lactam antibiotics useful for combating bacterial infections (including urinary tract infections and respiratory infections) in mammalian species, such as domesticated animals and humans.

The novel carboxy protecting group (derived from a compound of formula I) used in compounds of formulas II, IV and V is extremely acid labile, and because of this, its removal from a compound of formula II or IV is a simple operation.

The compounds of formula I can be prepared by first reacting N-hydroxyphthalimide with a 2-(lower alkoxy)propene to yield a compound having the formula

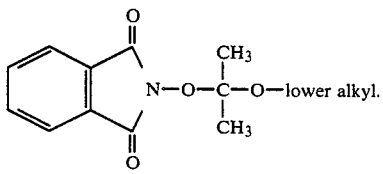

The reaction is preferably run in the presence of phosphorous oxychloride or pyridinium tosylate and an organic amine such as triethylamine or pyridine.

Conversion of an N-hydroxyphthalimide derivative of formula VI to the corresponding compound of formula I can be accomplished by treating the compound with hydrazine or an alkylhydrazine.

The compounds of formula II and IV can be obtained by first reacting a protected amino acid having the formula

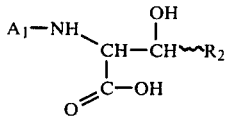

with a [(1-alkoxy-1-methyl)ethoxy]amine of formula I to yield the corresponding amide having the formula

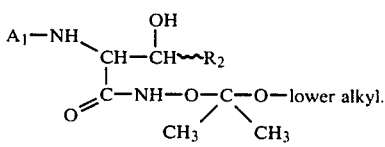

The reaction proceeds most readily if the protected amino acid of formula VII is first activated. Activated forms of carboxylic acids are well known in the art and include acid halides, acid anhydrides (including mixed acid anhydrides), activated acid amides and activated acid esters. Mixed acid anhydrides for use in the process of this invention can be formed from an amino acid of formula VII and a substituted phosphoric acid (such as dialkoxyphosphoric acid, dibenzyloxyphosphoric acid or diphenoxyphosphoric acid), a substituted phosphinic acid (such as diphenylphosphinic acid or dialkylphosphinic acid), dialkylphosphorous acid, sulfurous acid, thiosulfuric acid, sulfuric acid, a carboxylic acid such as 2,2-dimethylpropanoic acid, a carboxylic acid halide such as 2,2-dimethylpropanoyl chloride, and others. Exemplary of the activated amides which can be used in the process of this invention are those formed from an amino acid of formula VII and imidiazole, 4-substituted imidazoles, dimethylpyrazole, triazole, tetrazole or dimethylaminopyridine. Exemplary of the activated esters which can be used in the process of this invention are the cyanomethyl, methoxymethyl, dimethyliminomethyl, vinyl, propargyl, 4-nitrophenyl, 2,4-dinitrophenyl, trichlorophenyl, pentachlorophenyl, mesylphenyl, phenylazophenyl, phenylthio, 4-nitrophenylthio, p-cresylthio, carboxymethylthio, pyranyl, pyridinyl, piperidyl, and 8-quinolylthio esters. Additional examples of activated esters are esters with an N-hydroxy compound such as N,N-dimethylhydroxylamine, 1-hydroxy-2(1H)pyridone, N-hydroxysuccinimide, N-hydroxyphthalimide, and 1-hydroxy-6-chloro-1H-benzotriazole.

The amides of formula VIII which result from the coupling of an amino acid of formula VII and a [(1-alkoxy-1-methyl)ethoxy]amine of formula I can be cyclized by first converting the hydroxyl group to a leaving group, yielding a compound having the formula

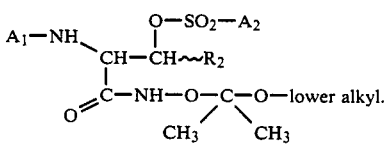

The conversion is accomplished by reacting a compound of formula VIII with a compound having the formula $$A_2-SO_2-X \qquad\qquad X$$

wherein X is chlorine or bromine and $A_2$ is alkyl, phenyl or substituted phenyl (preferably methyl or p-methylphenyl). The reaction can be run in an organic solvent (e.g., pyridine or dichloromethane) in the presence of an organic base (e.g., triethylamine).

Cyclization of a compound of formula IX to the corresponding 2-azetidinone of formula IV can be accomplished by treating a compound of formula IX with a base such as an alkali metal carbonate, bicarbonate or hydroxide; or a quaternary ammonium carbonate, bicarbonate, or hydroxide. The reaction is preferably carried out in water or a mixture of water and an organic solvent.

Alternatively, the 2-azetidinones of formula IV can be prepared directly from the corresponding compounds of formula VIII without first converting the hydroxyl group to a leaving group. Treatment of a compound of formula VIII with triphenylphosphine and diethylazodicarboxylate yields a compound of formula IV.

Both of the methods disclosed above for ring closure of a compound of formula VIII result in the inversion of the stereochemistry of the $R_2$ substituent.

Deprotection of the amino group of a compound of formula IV to obtain the corresponding compound of formula V can be accomplished using known procedures that will depend on the particular protecting group ($A_1$) being removed. Treatment with hydrogen (using a catalyst such as palladium) cleaves a phenylmethoxycarbonyl or substituted phenymethoxycarbonyl protecting group.

Well known acylation techniques can be used to convert a compound of formula V to a compound of formula II. Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxyl groups) it may be necessary to first protect these functional groups, then carry out the acylation reaction, and finally deprotect the resulting product.

The [(1-alkoxy-1-methyl)ethoxy]amino protecting group can be readily cleaved from a compound of formula II or IV by treatment of the compound with acid.

Additional methodology for preparing the novel compounds of formulas II and IV will be apparent to the practitioner of this invention. For example, a compound of formula IX can have its amino protecting group ("$A_1$") cleaved and the resulting amino compound acylated prior to cyclization and cleavage of the [(1-alkoxy-1-methyl)ethoxy]amino protecting group. Still additional methodology comprises starting with an acylated amino acid having the formula

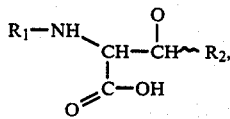

XI reacting it with a [(1-alkoxy-1-methyl)ethoxy]amine of formula I, cyclizing the resulting amide and the cleaving the [(1-alkoxy-1-methyl)ethoxy]amino protecting group.

The following examples are specific embodiments of this invention.

Example 1

[(1-Methoxy-1-methyl)ethoxy]amine (A) N-[1-Methoxy-1-methyl)ethoxy]phthalimide

N-Hydroxyphthalimide (40.7 g, 0.25 mol) was suspended in 160 ml of dry tetrahydrofuran. 2-Methoxypropene (36 ml, 0.375 mol) was added followed by 1 drop of phosporous oxychloride. After 40 minutes, the solid had dissolved. Triethylamine (2 ml) was added and the tetrahydrofuran was evaporated. The residue was taken up in 500 ml of ethyl acetate, filtered, washed with aqueous sodium bicarbonate and then saturated aqueous sodium chloride, and dried over sodium sulfate. The solvent was removed and the white solid residue was dried under vacuum to afford 53.6 g of the title compound.

(B) [(1-Methoxy-1-methyl)ethoxy]amine

N-[1-Methoxy-1-methyl)ethoxy]phthalimide (80.4 g, 0.342 mol) was dissolved in 500 ml of dichloromethane. The mixture was cooled in an ice/water bath and stirred mechanically. Methyl hydrazine (27.5 ml, 0.513 mol) was added over 15 minutes. After an additional 15 minutes, the cold bath was removed and the mixture was stirred for 1 hour. The mixture was filtered, concentrated to a small volume, filtered again, and distilled under vacuum (60°–70° C., 20 mm of Hg) to afford 27.3 g of the title compound as a colorless liquid.

Example 2

[3S-[3α(Z),4β]]-3-[[(2-Amino-4-thiazolyl)(methoxy imino)acetyl]amino]-1-hydroxy-4-methyl-2-azetidinone (A)
$N^2$-[(Phenylmethoxy)carbonyl]-N-[(1-methoxy-1-methyl)ethoxy]-L-threoninamide A solution of 171.5 g (0.677 mole) of N-[(phenylmethoxy)carbonyl]-L-threonine, 68.7 g (0.679 mole) of triethylamine and 6.8 g (0.086 mole) of pyridine in 1600 ml of dichloromethane was coled to −20° C. and 82.0 g (0.680 mole)of pivaloyl chloride was added dropwise. After stirring for 15 minutes, 85.3 g (0.812 mole) of [(1-methoxy-1-methyl)ethoxy]amine was added dropwise. After stirring for 30 minutes, the mixture was warmed to −15° C. and a solution of 101.7 g (1.211 mole) of sodium carbonate in 1 liter of water was added. The reaction mixture was allowed to warm to room temperature and the organic layer was separated. The aqueous solution was extracted with 400 ml of dichloromethane and the combined organic layers were dried with sodium sulfate. The solvent was concentrated to 400 ml and 1.5 liters of ethyl acetate was added. The solution was concentrated to 500 ml and after the addition of 50 ml of petroleum ether, the title compound started to crystallize. It was filtered off, washed with petroleum ether and dried in vacuo, yielding 215.2 g of the title compound, melting point 88° C.

(B)
(3S-trans)-3-[[(Phenylmethoxy)carbonyl]amino]-1-[(1-methoxy-1-methyl)ethoxy]-4-methyl-2-azetidinone A solution of 20.4 g (60 mmole) of N²-[(phenylmethoxy)carbonyl]-N-[(1-methoxy-1-methyl)ethoxy]-L-threoninamide and 6.1 g (60 mmole) of triethylamine in 200 ml of ethyl acetate was cooled to −2° C., and 6.9 g (60 mmole) of methanesulfonyl chloride was added dropwise. After stirring for one hour, the mixture was washed with ice-cold water, sodium bicarbonate and brine. The solution was filtered over Hyflo, and 24 g (174 mmole) of potassium carbonate was added. After stirring overnight at ambient temperature, the potassium carbonate was filtered off, and the filtrate washed with ice-cold sodium bicarbonate and brine, dried with sodium sulfate and evaporated to dryness, yielding 17.8 g of the title compound as a slightly yellow oil.

(C)
[3S-[3α(Z),4β]]-3-[[(2-Amino-4-thiazolyl)-(methoxyimino)acetyl]amino]-1-[(1-methoxy-1methyl)ethoxy]-4-methyl-2-azetidinone (3S-trans)-3-[[(Phenylmethoxy)carbonyl]amino]1-[(1-methoxy-1-methyl)ethoxy]-4-methyl-2-azetidinone (9.0 g, 27.9 mmole) was dissolved in 100 ml of dimethylformamide, and 2.0 g of 10% palladium on charcoal was added. Hydrogen was bubbled through the mixture for one hour at ambient temperature and the catalyst filtered off. (Z)-2-Amino-4-thiazoleacetic acid (5.7 g, 27.9 mmole), 0.5 g (3 mmole) of N-hydroxybenzotriazole and 6.3 g (30.6 mmole) of dicyclohexylcarbodiimide were added to the filtrate and the resulting mixture was stirred for three hours at amibent temperature. The solvent was evaporated in vacuo and the residue was taken up in ethyl acetate. After washing with cold sodium bicarbonate and brine, the organic layer was dried with sodium sulfate and evaporated in vacuo. The residue was purified by column chromatography on silica gel using ethyl acetate as solvent, and yielding 4.0 g of the title compound, melting point 101° C., dec.

(D)
[3S-[3α(Z),4β]]-3-[[(2-Amino-4-thiazolyl)(methoxyimino)acetyl]amino]-1-hydroxy-4-methyl-2-azetidinone

[3S-[3α(Z),4β]]-3-[[(2-Amino-4-thiazolyl)(methoxyimino)acetyl]amino]-1-[(1-methoxy-1methyl)ethoxy]-4-methyl-2-azetidinone (0.53 g) was dissolved in 2 ml of methanol, and 10 ml of water was added. The pH was adjusted to 3.0 by adding 1N hydrochloric acid, and the mixture was stirred for 10 minutes at room temperature. The methanol was evaporated in vacuo, and the resulting aqueous solution freeze-dried yielding 0.43 g of the title compound, melting point 188° C., dec.

Example 3
(3S)-3-[[(Phenylmethoxy)carbonyl]amino]-1-hydroxy-2-azetidinone (A)
N²-[(Phenylmethoxy)carbonyl]-N-[(1-methoxy-1-methyl)ethoxy]serinamide N-[(Phenylmethoxy)carbonyl]serine (47.8 g, 0.2 mol) was dissolved in 440 ml of dichloromethane by the addition of triethylamine (20.2 g, 0.2 mol) and pyridine (2 g, 0.025 mol). The mixture was cooled to −20° C. and pivaloyl chloride (24.2 g, 0.2 mol) was added dropwise within 20 minutes. After 15 minutes, stirring at −20° C., [(1-methoxy-1-methyl)ethoxy]amine (25.2 g, 0.24 mol) was added at −20° C. The mixture was stirred for 30 minutes at −20° C. and then added to a solution of sodium bicarbonate (30 g, 0.36 mol) in 300 ml of water. The temperature rose to 5° C. and the pH was greater than 7.2. After 15 minutes, the organic layer was separated and the aqueous layer was extracted with 50 ml of dichloromethane. The solvent was removed in vacuo to a 50 ml volume, 400 ml of ethyl acetate was added and the solvent was removed again to a 100 ml volume. Addition of some seeds was followed by evaporating to a 50 ml volume. The resulting white crystals were isolated by filtration and dried to afford 45.9 g of the title compound, melting point 96°-98° C.

(B)
(3S)-3-[[(Phenylmethoxy)carbonyl]amino]-1-hydroxy-2-azetidinone

N²-[(Phenylmethoxy)carbonyl]-N-[(1-methoxy-1-methyl)ethoxy]serinamide (32.6 g, 0.1 mol) was suspended in 500 ml of ethyl acetate. After cooling to 0° to −5° C., triethylamine (13.1 g, 0.13 mol) was added followed by dropwise addition of methanesulfonyl chloride (14.7 g, 0.12 mol) within 15 minutes. The temperature did not exceed 0° C. After 1 hour at 0° C. to −5° C., the reaction was complete.

Hydrazine hydrate (3.3 ml) was added and the mixture was stirred for 30 minutes at 0° C. The mixture was washed with 200 ml of water, two 180 ml portions of aqueous monobasic sodium phosphate solution (100 g/l) and 80 ml of brine. Potassium carbonate (40 g) was added to the solution of mesylated material in ethyl acetate and the mixture was stirred overnight at 20° C. When the reaction had finished, it was filtered clear. Water (16 ml) and 21 ml of methanol were added to the solution. The mixture was acidified to pH 1 with 1N hydrochloric acid (ca. 25 ml), and about 40 ml of methanol was added to get a clear solution. After stirring for 4 hours at 20° C., the reaction had finished. The mixture was washed twice with 100 ml of brine, then extracted with three 140 ml portions of aqueous potassium hydroxide (100 g/l) at 20° C. The aqueous layer was acidified with conc. hydrochloric acid (ca. 50 ml) to get a pH of 2.3 and stirred for 30 minutes. The precipitate was filtered, washed with water and dried at 40° C. to afford 17.2 g of the title compound, melting point 122°-123° C., dec.

Example 4
(3S-cis)-3-[[(Phenylmethoxy)carbonyl]amino]-1[(1-methoxy-1-methyl)ethoxy]-4-methyl-2- azetidinone (A)
N²-[(Phenylmethoxy)carbonyl]-N-[(1-methoxy-1-methyl)ethoxy]allothreoninamide Following the procedure of example 2A, but substituting allothreonine for L-threonine, yielded the title compound.

(B)
(3S-cis)-3-[[(Phenylmethoxy)carbonyl]amino]-1[(1-methoxy-1-methyl)ethoxy]-4-methyl-2-azetidinone N²-[(Phenylmethoxy)carbonyl]-N-[(1-methoxy-1-methyl)ethoxy]allothreoninamide (238.6 g, 0.731 mol) was suspended in 2.5 l of ethyl acetate. After cooling to −2° C., triethylamine (103.5 g, 1.022 mol) was added followed by the dropwise addition of methanesulfonyl chloride (117.2 g, 1.022 mol). After 1 hour at 0° C., hydrazine hydrate (14.2 ml) was added and the mixture was stirred for 45 minutes at 0° C. The mixture was washed with water, aqueous monobasic sodium phosphate solution (100 g/l) and brine.

Potassium carbonate (292.5 g) was added to the solution and the mixture was stirred overnight at ambient temperature. After filtration, 290 ml of water and 370 ml of methanol were added, and the mixture was adjusted to pH 1 by adding 2 N hydrochloric acid. After stirring for two hours at ambient temperature, the mixture was washed with brine and water. Water (800 ml) was added and the pH was adjusted to 8.5 by the addition of an aqueous potassium hydroxide solution (100 g/l). The aqueous solution was separated and adjusted to pH 2.5 by the addition of concentrated hydrochloric acid. The precipitate was filtered off, washed with water and dried in vacuo, yielding 95.2 g of the title compound, melting point 133° C.

What is claimed is:

1. A compound having the formula

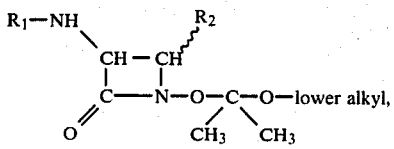

wherein $R_1$ is an acyl group derived from a carboxylic acid and $R_2$ is hydrogen, lower alkyl or carbamoyloxymethyl.

2. A compound in accordance with claim 1 wherein $R_2$ is methyl.

3. a compound in accordance with claim 1 wherein $R_2$ is carbamoyloxymethyl.

4. A compound in accordance with claim 1 having the formula

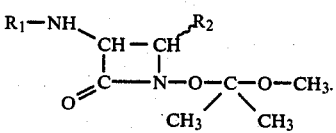

5. A compound in accordance with claim 1 wherein $R_1$ is

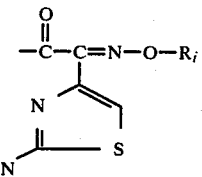

and $R_i$ is methyl, ethyl, carboxymethyl, 1-carboxy-1-methylethyl, 2,2,2-trifluoroethyl or 1-carboxycyclopropyl.

6. A compound in accordance with claim 1 wherein $R_1$ is

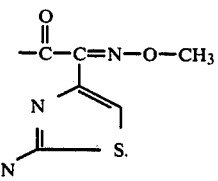

7. A compound in accordance with claim 1 wherein $R_1$ is

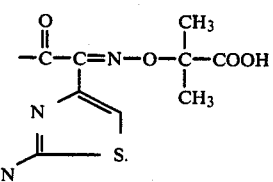

8. A compound in accordance with claim 1 wherein $R_1$ is phenylmethoxycarbonyl, (4-methoxyphenyl)methoxycarbonyl, (4-chlorophenyl)methoxycarbonyl, (4-methylphenyl)methoxycarbonyl, (2-methylphenyl)methoxycarbonyl, (3-methylphenyl)methoxycarbonyl, (2,4,6-trimethylphenyl)methoxycarbonyl, (3,5-dimethoxyphenyl)methoxycarbonyl, (2-nitrophenyl)methoxycarbonyl, (4-nitrophenyl)methoxycarbonyl, allyloxycarbonyl, cinnamyloxycarbonyl, vinyloxycarbonyl, 1,1-dimethylpropynyloxycarbonyl, 2-furanylmethyloxycarbonyl, 2-methylthioethyloxycarbonyl, 2-trimethylsilylethyloxycarbonyl, 2-methylsulfonylethyloxycarbonyl, 9-fluorenylmethyloxycarbonyl, 2,2,2-trichloroethyloxycarbonyl, 2-cyanoethyloxycarbonyl, or 1,1-dimethyl-2-cyanoethyloxycarbonyl.

9. A compound in accordance with claim 1 wherein $R_2$ is hydrogen.

* * * * *